(12) United States Patent
Chao et al.

(10) Patent No.: US 11,753,634 B2
(45) Date of Patent: Sep. 12, 2023

(54) METHOD AND APPARATUS FOR APPLYING HEAT TO LIVING TISSUE

(71) Applicant: NATIONAL TAIWAN UNIVERSITY, Taipei (TW)

(72) Inventors: Chih-Yu Chao, Taipei (TW); Wei-Ting Chen, Taipei (TW); Chueh-Hsuan Lu, Taipei (TW); Chih-Hsiung Hsieh, Taipei (TW); Yu-Yi Kuo, Taipei (TW); Guan-Bo Lin, Taipei (TW); Yi-Kun Sun, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 609 days.

(21) Appl. No.: 16/739,746

(22) Filed: Jan. 10, 2020

(65) Prior Publication Data
US 2021/0180040 A1     Jun. 17, 2021

(30) Foreign Application Priority Data
Dec. 12, 2019   (TW) ............................... 108145555

(51) Int. Cl.
*A01N 1/02*      (2006.01)
*C12N 13/00*    (2006.01)
*C12N 5/071*    (2010.01)
*C12N 5/0793*  (2010.01)

(52) U.S. Cl.
CPC ............ *C12N 13/00* (2013.01); *A01N 1/0284* (2013.01); *C12N 5/0619* (2013.01); *C12N 5/0697* (2013.01)

(58) Field of Classification Search
CPC .................................................. A01N 1/0284
See application file for complete search history.

(56) References Cited

FOREIGN PATENT DOCUMENTS

WO    WO 2018/169969 A1    9/2018

OTHER PUBLICATIONS

Lu et al., (2019) Thermal cycling-hyperthermia in combination with polyphenols, epigallocatechin gallate and chlorogenic acid, exerts synergistic anticancer effect against human pancreatic cancer PANC-1 cells. PLoS One 14(5): e0217676. https://doi.org/10.1371/journal.pone.0217676 . (Year: 2019).*

(Continued)

*Primary Examiner* — Kara D Johnson
(74) *Attorney, Agent, or Firm* — Birch, Stewart, Kolasch & Birch, LLP

(57) ABSTRACT

A method of applying heat to living tissue mainly uses a device for performing heat treatment on at least a portion of the living tissue in high-low-high temperature steps. In high temperature step, the temperature of the at least a portion of the living tissue is heated and kept between 39-46° C., and the heating period is no longer than 30 minutes. In low temperature step, the at least a portion of the living tissue is cooled, and the low temperature period should not be greater than a natural cooling time interval. In addition, the low temperature period must also be shorter than the heating period. Thus, the present invention allows the abnormal cells to be selectively restored or apoptotic without damaging the normal cells.

8 Claims, 12 Drawing Sheets

(56) References Cited

OTHER PUBLICATIONS

Chen et al., Thermal cycling as a novel thermal therapy to synergistically enhance the anticancer effect of propolis on PANC-1 cells. International Journal of Oncology, vol. 55, No. 33 (Jul. 16, 2019) pp. 617-628 (Year: 2019).*

Chen et al., "Thermal cycling as a novel thermal therapy to synergistically enhance the anticancer effect of propolis on PANC-1 cells", International Journal of Oncology, vol. 55, No. 3, pp. 617-628, 2019, Jul. 16, 2019.

Dreher et al., "Thermal Cycling Enhances the Accumulation of a Temperature-Sensitive Biopolymer in Solid Tumors", Cancer Res 2007, 67: (9), May 1, 2007, pp. 4418-4424.

Lu et al., "Application of non-invasive low-intensity pulsed electric field with thermal cycling-hyperthermia for synergistically enhanced anticancer effect of chlorogenic acid on PANC-1 cells", BioRxiv 745562, 2019, Aug. 23, 2019, total 45 pages.

Lu et al., "Thermal cycling-hyperthermia in combination with polyphenols, epigallocatechin gallate and chlorogenic acid, exerts synergistic anticancer effect against human pancreatic cancer PANC-1 cells", BioRxiv 548552, 2019, Feb. 14, 2019, total 49 pages.

Lu et al., "Thermal cycling-hyperthermia in combination with polyphenols, epigallocatechin gallate and chlorogenic acid, exerts synergistic anticancer effect against human pancreatic cancer PANC-1 cells", Plos One 14(5): e0217676, 2019, May 31, 2019, pp. 1-18.

* cited by examiner

METHOD AND APPARATUS FOR APPLYING HEAT TO LIVING TISSUE

BACKGROUND OF THE INVENTION

1. Technical Field

The present invention relates to a technique of performing heat treatment on living tissue, in particular, to a method and an apparatus for applying heat to living tissue.

2. Description of Related Art

In the presently known arts, the primary purpose of the technique of performing heat treatment on living tissue is to apply heat to cancer cells. With the utilization of the characteristic of cancer cells being relatively more sensitive to heat, the effect of apoptosis of cancer cells can be achieved. However, regarding the presently known heating technique for cancel cells, typically, during the heating process, the normal cells are apoptotic together with the cancel cells. Consequently, presently, there is no effective method capable of achieving: a technique capable of effectively causing the apoptosis of cancer cells while preserving the survival of normal cells at the same time.

WIPO Patent WO 2018/169969 A1 discloses a process utilizing pulsed energy to heat treat biological tissue, and it mainly discloses the use of heating and interrupted heating cycles on cells, and during the heating, the cells are able to generate heat shock protein in order to improve the treatment effect. In addition, the halted period without heating needs to be longer than the heating period, thereby increasing the heat shock protein quantity in the cells without damaging the cells.

The aforementioned technique is mainly used in treatment, and the halted period without heating needs to be longer than the heating period. Despite that such technique can be used in the treatment of living tissue, nonetheless, the technique of heating period and halted period are not applicable to cause the apoptosis of cancer cells. Furthermore, for both normal cells and abnormal cells (i.e. cancer cells), there are no techniques capable of performing treatment or causing apoptosis of cancer cells while preserving the normal cells without damages at the same time. Moreover, the halted period needs to be longer than the heating period, for living tissue, overly long halted period can cause the transmission of biochemical signals and protein expressions stimulated by thermal stress in the living tissue to be interrupted, thus leading to the interruption of cell repair continuity. As a result, there are rooms for improvement for the aforementioned technique.

In the journal of Cancer Res 2007; 67 (9) 4418 (May 1, 2007), the article of "Thermal Cycling Enhances the Accumulation of a Temperature-Sensitive Biopolymer in Solid Tumors" discloses that a technique of heating and interrupted heating of cells. FIG. 5 of the article discloses the technique of heating-cooling between the temperature of 41.5° C. and 37° C. Its heating effect is to allow the microparticle mass of macromolecular carrier in the tumor vasculature to become large, thereby explaining that anti-cancer drug could be delivered into the cancer tissue via the micron-sized particles of macromolecular carrier. Nevertheless, this article publication does not explain the reason why the heating period needs to be longer than the cooling period. In addition, the heating subject matter is the microparticles of macromolecular carrier, which is not directly related to the technique of performing heat treatment on living tissue in order to allow the normal cells to maintain their viability while causing the apoptosis or restoration of abnormal cells.

BRIEF SUMMARY OF THE INVENTION

A primary objective of the present invention is to provide a method and an apparatus for applying heat to living tissue, and it is able to selectively restore abnormal cells under the condition where the normal cells are prevented from damages.

To achieve the aforementioned objective, the present invention provides a method for applying heat to living tissue, comprising the following steps: S1) high temperature: in a first time interval, heat at least a portion of a living tissue, and maintain a temperature of the at least a portion of the living tissue between 39-46° C. within a first effective time interval; the first time interval being less than 30 minutes; wherein the at least a portion of the living tissue includes a plurality of normal cells and a plurality of abnormal cells, and the abnormal cells refer to ill-conditioned cells; S2) low temperature: use an end-time point of the first time interval as a starting point of a second time interval, and cool the at least a portion of the living tissue in the second time interval; and a temperature of the least a portion of the living tissue in the second time interval being lower than a maximum temperature in the first time interval; and a time period required for the at least a portion of the living tissue to be cooled from 45° C. to 39° C. via a natural cooling method under a criteria where an environmental temperature is between 36.5-37° C. being defined to be a natural cooling time interval; the second time interval being shorter than the natural cooling time interval; and S3) high temperature: use an end-time point of the second time interval as a starting point of a third time interval, and heat the at least a portion of the living tissue in the third time interval in order to increase a temperature of the at least a portion of the living tissue, and maintain the temperature of the at least a portion of the living tissue to be between 39-46° C. in a third effective time interval; the third time interval being less than 30 minutes; the second time interval being shorter than the first time interval, and the second time interval being shorter than the third time interval.

With the aforementioned steps: the method provided by the present invention is able to selectively restore abnormal cells under the condition where normal cells are not damaged.

Preferably in step S1) and step S3), a predefined compound or natural complex can be further applied to the at least a portion of the living tissue.

Accordingly, the method provided by the present invention is able to selectively cause the apoptosis of abnormal cells under the condition where normal cells are not damaged.

In addition, the present invention further provides an apparatus using the aforementioned method, comprising: a microcomputer; a nonvolatile memory electrically connected to the microcomputer and having a heat treatment logic stored therein in order to be executed by the microcomputer; a heating device electrically connected to the microcomputer; and a temperature sensor electrically connected to the microcomputer and used to detect a current temperature of the at least a portion of the living tissue; wherein the heat treatment logic comprises technical features of the step S1) to step S3), and when the microcomputer executes the heat treatment logic, it executes methods of the step S1) to step S3), and the microcomputer also controls the heating device in heating the at least a portion of the living tissue when there is a need to perform heating.

With the aforementioned device, the present invention is able to perform the steps of the aforementioned method on the at least a portion of the living tissue in order to achieve the aforementioned effect of selectively allowing abnormal cells to be apoptotic or restored under the condition where the normal cells are not damaged.

DETAILED DESCRIPTION OF THE INVENTION

To explain the technical features of the present invention, the following provides detailed description of the preferred embodiments along with the accompanying drawings.

Figure 1:
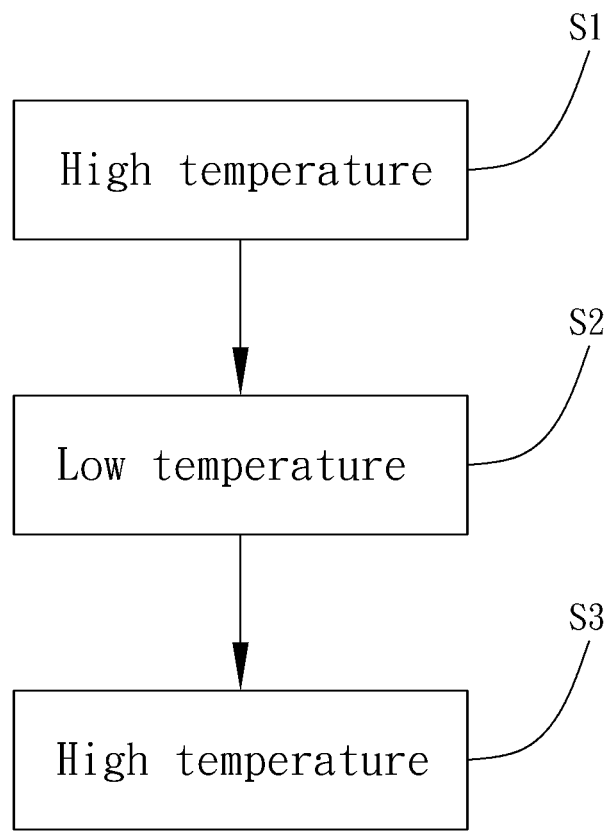
FIG. 1 is a flowchart according to the first preferred embodiment of the present invention.
Figure 2:
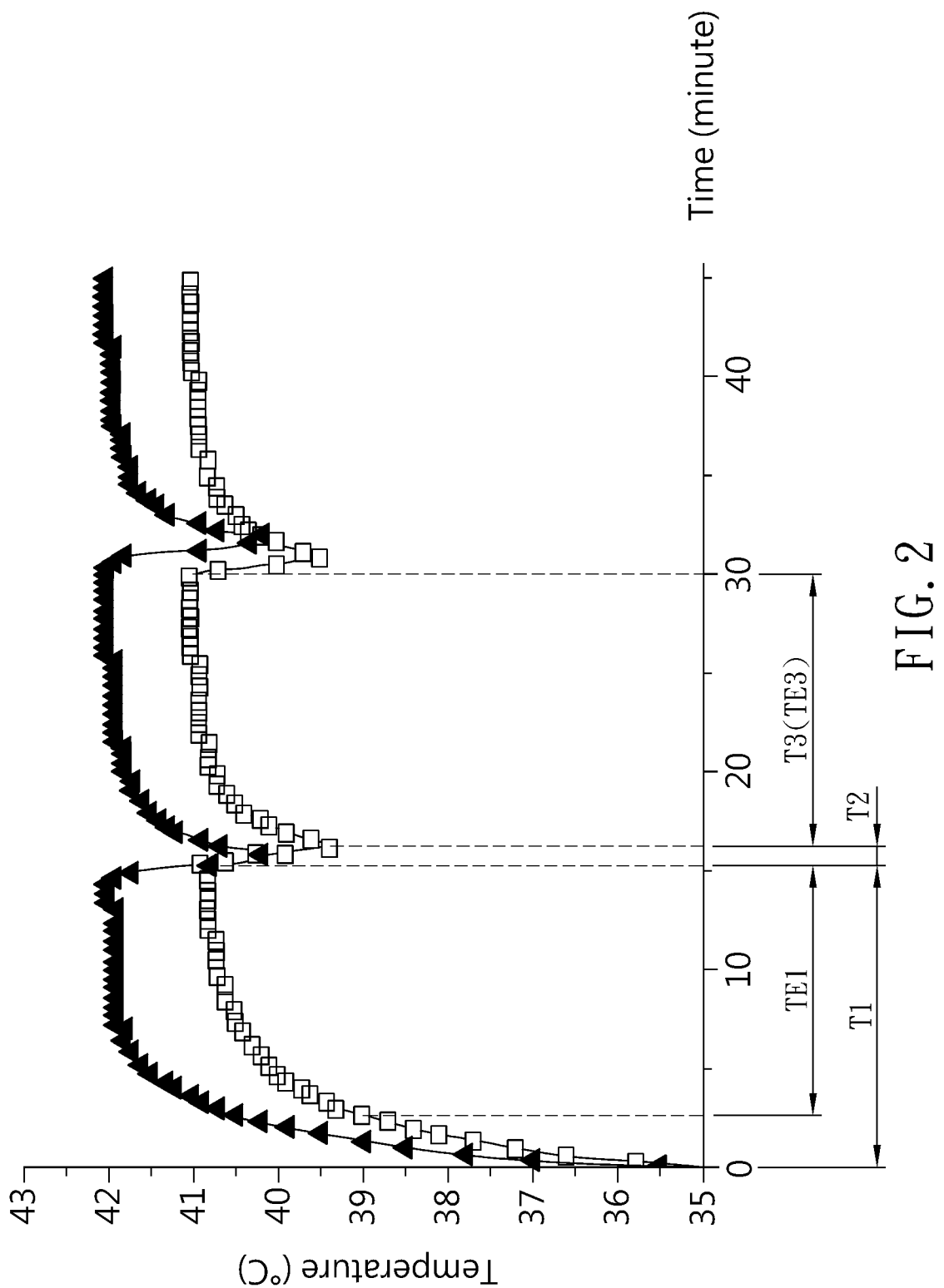
FIG. 2 is a temperature-time relation graph according to the first preferred embodiment of the present invention.

As shown in FIG. 1 to FIG. 6, the present invention provides a method for applying heat to living tissue according to a first preferred embodiment of the present invention, and the method mainly comprises the following steps:

S1) high temperature: As shown in FIG. 2, heating is performed on a portion (not shown in the drawings) of a living tissue in a first time interval T1, and the temperature of the portion of the living tissue is maintained between 39-46° C. in a first effective time interval TE1. The first time interval T1 is less than 30 minutes, wherein the portion of the living tissue includes a plurality of normal cells and a plurality of abnormal cells. The abnormal cells refer to ill-conditioned cells. When the living tissue is small, the entire living tissue can also be heated directly. During the actual implementation, the portion of the living tissue can be a portion existing on the nerve of human body or can be a portion of survival nerve cultured in the petri dish obtained from human body biopsy, or may be biopsy obtained from laboratory animal, such as laboratory rat. In the first embodiment, human neuroblastoma cells (SH-SY5Y) under degenerative state are used as an example for illustration. In this embodiment, hydrogen peroxide ($H_2O_2$) is used to treat the human neural cells (SH-SY5Y) cultured in the petri dish (not shown in the drawings) with a culture solution. Under the high oxidative stress of the hydrogen peroxide, a portion of the neural cells becomes degenerative or ill-conditioned abnormal cells under damaged state. Regarding the heating method, high intensity focused ultrasound (HIFU), water bath, infrared device, radio frequency electromagnetic wave or microwave can be used to perform heating. The use of HIFU is able to penetrate through the body surface to perform heating on a portion of the human tissue underneath the body surface without damaging the body surface and other tissue regions in the body. In addition, the size of the focal point of HIFU can be adjusted to control the range of heating. Nevertheless, in this embodiment, the water bath method is used as an example for illustration. Furthermore, during the heating process, the power can be adjusted to continue the heating, and the heat pulse method can also be used to perform heating. By adjusting the pulse repetition rate or other parameters, the overall heat energy can be adjusted in order to maintain the temperature of the object being heated within a certain range.

In addition, in this step S1), since the portion of the living tissue is in the petri dish before heating, consequently, its temperature before heating is the same as the petri dish temperature such it is at the temperature of 37° C. under normal condition. Furthermore, after heating the portion of the living tissue, before its temperature is increased to 39° C., it is not yet entering the first effective time interval TE1. In the first embodiment, the human neural cells (SH-SY5Y) are used as an example for illustration, and the line connected by the rectangular dots in FIG. 2 refers to the heating method with the maximum heating temperature of 40.9° C., and the water bath method is used as an example of the heating method for illustration. Accordingly, the time point when the portion of the living tissue is heated and the temperature is increased to 39° C. is considered as the starting point of the first effective time interval TE1. Subsequently, heating continues until the temperature reaches 40.9° C. in the first effective time interval TE1 and its temperature is maintained such that the temperature is in between 39-46° C. In the first embodiment, as shown in FIG. 2, the first time interval T1 is 15 minutes, and the first effective time interval TE1 is 13 minutes.

It shall be noted that in the aforementioned first effective time interval TE1, during the heating of the living tissue, it is preferable that the temperature of the living tissue while heating is less than 46° C.; otherwise, apoptosis of the cells may occur. In addition, when living tissue is heated to reach the temperature above 39° C., its cells are subject to heat stress. Accordingly, the first time interval T1 is chosen to be within 30 minutes in order to prevent damages on the living cells due to overly long period of continuous heating under heat stress. In the above description of this embodiment, the first time interval T1 is 15 minutes, and the portion of the living tissue is heated to 40.9° C. and maintained at 40.9° C. Consequently, it is within the safe range while producing appropriate heat stress to be generated on all of the cells in the portion of the living tissue in order to allow appropriate heat stress to promote the repairment and restoration of damaged neural cells.

S2) low temperature: The end-time point of the first time interval T1 is used as the starting point of a second time interval T2. During the second time interval T2, the portion of the living tissue is cooled, and the temperature of the portion of the living tissue in the second time interval T2 is lower than the maximum temperature in the first time interval T1. In addition, a time period required for the portion of the living tissue to be cooled from 45° C. to 39° C. via a natural cooling method under the criteria where an environmental temperature is between 36.5-37° C. is defined to be a natural cooling time interval TM. The second time interval T2 is shorter than the natural cooling time interval TM. Regarding the aforementioned cooling, during the actual practice, it can use the natural cooling method. That is, no heating or cooling is performed but allowing the portion of the living tissue to be cooled naturally in the second time interval T2. In other cooling methods, the technique of refrigeration method can be used for cooling, such as a temperature-controlled circulating coolant can be used or mild heating can be performed with a power lower than the heating power in the aforementioned first time interval T1, thus causing the portion of the living tissue not being maintained at the original temperature due to insufficient heating power, thereby resulting in a decrease of temperature.

Figure 3:
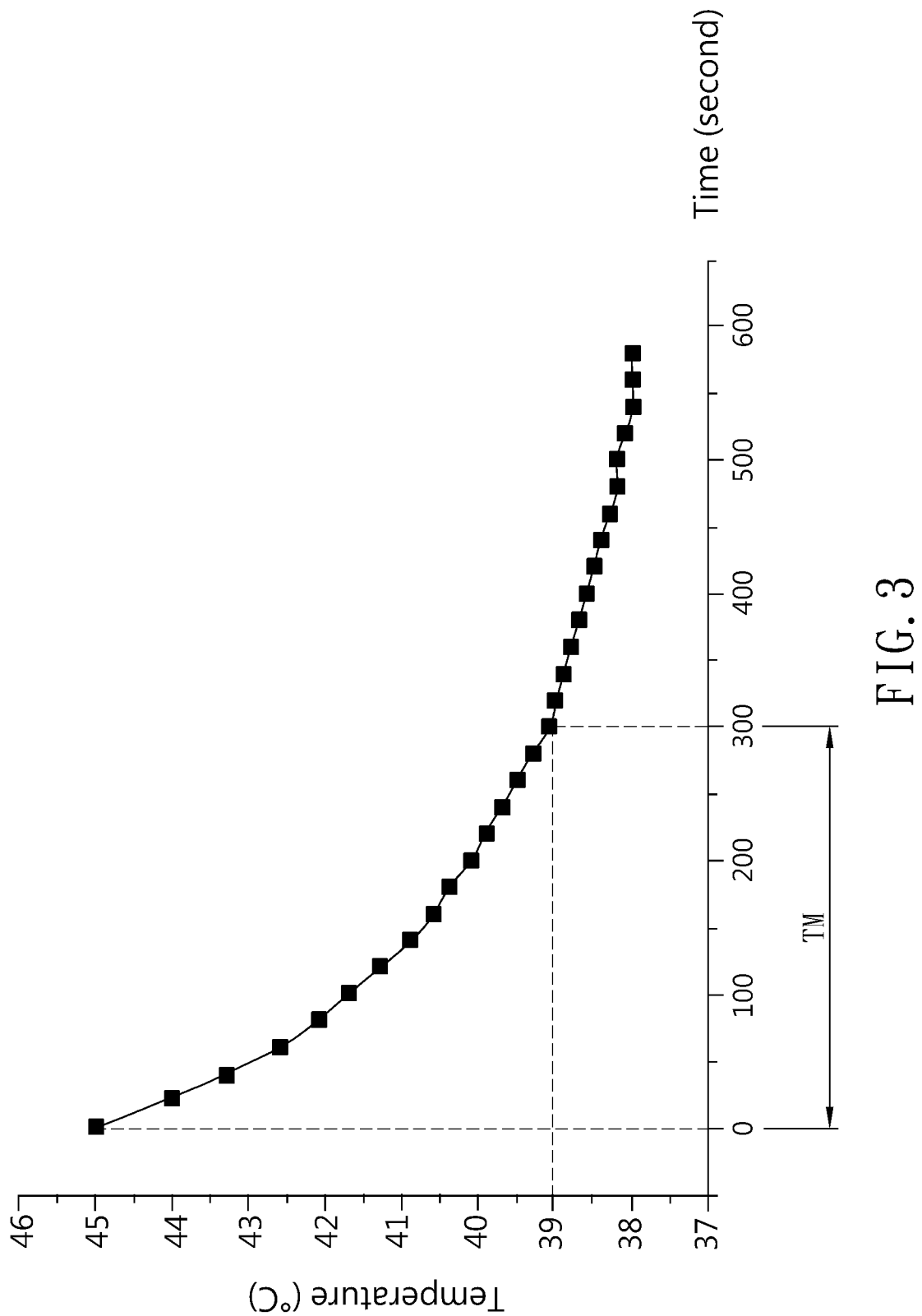
FIG. 3 is a natural cooling time interval diagram according to the first preferred embodiment of the present invention.

Furthermore, in the aforementioned step S2), since the living cells cannot be heated continuously; otherwise the living cells may be damaged after an overly long period of heating time, or leading to greater damage of the already damaged living cells. Consequently, there is a need for the existence of a low temperature stage after the high temperature stage in order to allow the living cells to be relieved from heating, and such low temperature stage refers to the second time interval T2, which is also the relief time for the living cells after heating. In addition, the second time interval T2 cannot be too long. Since the high temperature stage is to stimulate the cell protection effect when the living cells are subject to an appropriate heat stress, thereby allowing damaged cells to be repaired for restoration, if the low temperature stage is of an overly long period of time (i.e. providing an excessive relief for the living cells after heating), the transmission of the biochemical signals and protein expressions stimulated by thermal stress in the living cells can be interrupted, leading to the interruption of cell repair continuity. In view of the aforementioned criteria along with the consideration that living cells are not being affected by the heat stress at the condition where the temperature is lower than 39° C., the inventor of the present invention believes that under the condition where the environmental temperature or the temperature of the culture solution is close to the body temperature of 36.5-37° C., the time required for the portion of the living tissue to be cooled from 45° C. to 39° C. via the natural cooling method is the maximum possible low temperature period. If such time is exceeded, then the problem of interruption of cell repair continuity due to the interrupted transmission of biochemical signals in the living tissue is very likely to occur. Accordingly, in the present invention, such period of time is defined to be the natural cooling time interval TM. In addition, through experiments conducted by the inventor, the result obtained for such time interval TM is 5 minutes, as shown in FIG. 3. Since the natural cooling time interval TM is the longest low temperature period, consequently, the second time interval T2 needs to be shorter than the natural cooling time interval TM. In the first embodiment, the second time interval T2 is 45 seconds.

Regarding the temperature of the portion of the living tissue at the end of the first time interval T1 in step S1), in comparison to the temperature of the portion of the living tissue at the end of the second time interval T2 in step S2), it shall be at least higher by more than 0.5° C., in order to cause the portion of the living tissue to have changes under the heat stress of different temperatures. In the first embodiment, as shown in FIG. 2, when the second time interval T2 is ended, the temperature of the portion of the living tissue is 39.4° C., and when then first time interval T1 is ended, the temperature of the portion of the living tissue is 40.9° C. The two temperatures differ by 1.5° C.

S3) high temperature: The end-time point of the second time interval T2 is used as a starting point of a third time interval T3, and the portion of the living tissue in the third time interval is heated in order to increase the temperature of the portion of the living tissue. Since the temperature in step S2) is not reduced to lower than 39° C. but is at 39.4° C., which is higher than 39° C., the third time interval T3 is equivalent to that the entire heating period is the third effective time interval TE3. Subsequently, heating is continued in the third time interval T3 until the temperature reaches 40.9° C. and such temperature is maintained. Furthermore, such temperature is in between 39-46° C. The third time interval T3 is less than 30 minutes. In the first embodiment, as shown in FIG. 2, the third time interval T3 is 15 minutes, and the third effective time interval TE3 is 13 minutes. Moreover, the second time interval T2 is shorter than the first time interval T1, and the second time interval T2 is shorter than the third time interval T3.

In the first embodiment, the third time interval T3 is of the same duration as the first time interval T1. In addition, the second time interval T2 is shorter than the first time interval T1 and the third time interval T3. In other words, the time when the portion of the living tissue is under high temperature needs to be longer than the time for low temperature. Consequently, it is able to ensure that the portion of the living tissue is subject to sufficient heat stress under appropriate heating period, and appropriate relief is provided in the time for low temperature after each heating. As a result, the aforementioned method of high temperature step, low temperature step and high temperature step again of the present invention is able to allow ill-conditioned or damaged cells in the portion of the living tissue to generate the restoration effect while preserving the survival of the original normal cells without damages.

It shall be further considered that the heating time cannot be too short. In other words, in the high temperature steps of step S1) and step S3), the heating time is preferably to be longer than 30 seconds, meaning that the first time interval T1 and the third time interval T3 are not shorter than 30 seconds in order to ensure that the portion of the living tissue is able to receive sufficient heat in order to increase to the required temperature. Furthermore, the time for low temperature cannot be too short. In other words, in the low temperature step of step S2), the second time interval T2 cannot be shorter than 5 seconds in order to ensure that cooling relief after heating of the portion of the living tissue is effective.

Figure 4:
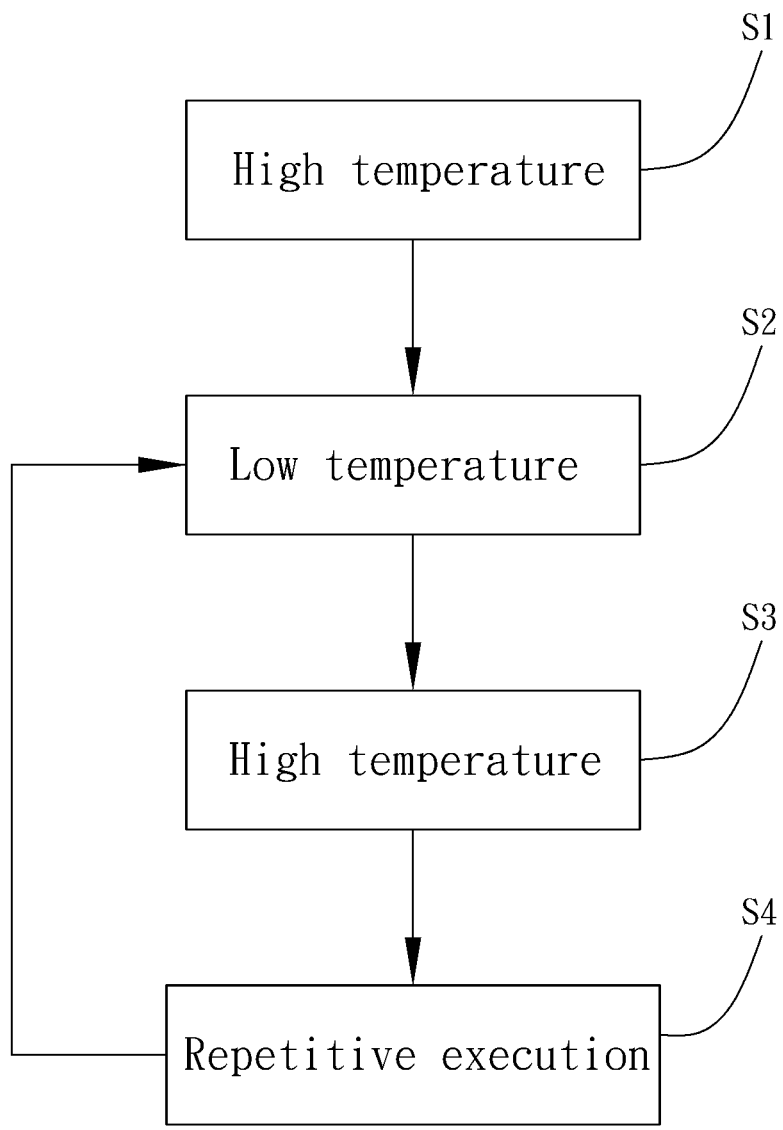
FIG. 4 is another flowchart according to the first preferred embodiment of the present invention.

According to the above, it can be understood that step S1) to step S3) refer to a cyclic type of heat treatment method from high temperature step to low temperature step, followed by high temperature step again. In practice, the number of cycles of the high temperature-low temperature steps can be increased, and an actual implementation method can, as shown in FIG. 4, further repetitively execute step S4): repetitively execute step S2) and step S3) sequentially. In other words, after step S1), the cycle of one time of low temperature step and one time of high temperature step is executed repetitively. Such step S4) is mainly provided to illustrate that after step S1), the multiple times of cycles of low temperature-high temperature steps can be repeated.

Figure 5A:
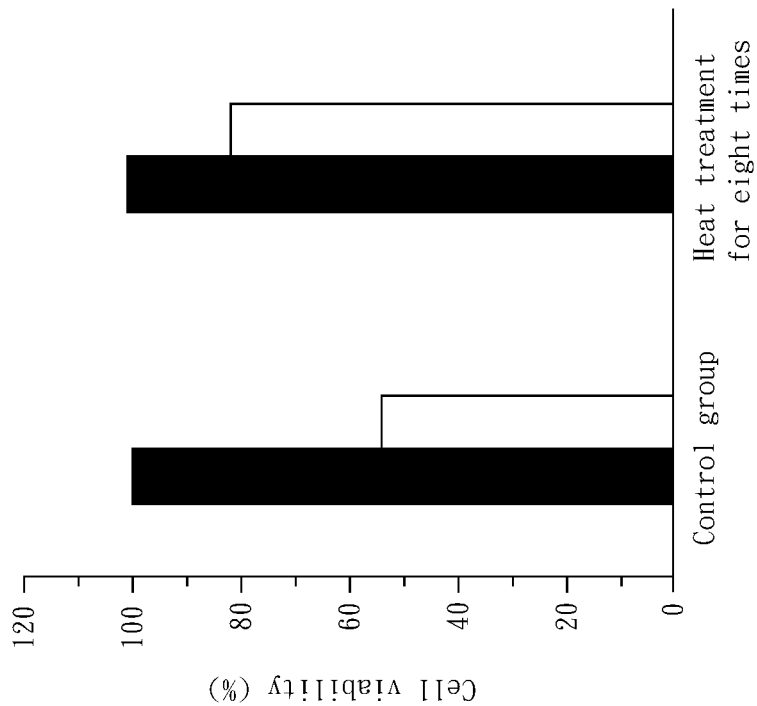
FIG. 5A is a cell viability diagram according to the first preferred embodiment of the present invention, showing the result of the human neural cells (SH-SY5Y) with/without application of hydrogen peroxide and heat treatment, and the maximum temperature of the heat treatment is 40.9° C.

After the aforementioned portion of the living tissue undergoes eight times of high temperature-low temperature steps, i.e. one time of step S1) with seven times of step S2) and step S3), the result is as shown in FIG. 5A, in which the black columns represent the cell viability of human neural cells (SH-SY5Y) without hydrogen peroxide treatment. By comparing the black column of the control group and the black column of the heating group with eight times of heat treatment in FIG. 5A, the cell viability of the normal neural cells is not affected after the heat treatment of the present invention, indicating that the heat treatment method of the present invention does not damage normal human neural cells (SH-SY5Y). The white column on the right side in FIG. 5A refers to the cell viability of the portion of the living tissue after the heat treatment and the hydrogen peroxide processing. Here, the control group represents the comparison group not subject to the heat treatment executed according to the method of the present invention. In FIG. 5A, the eight times of heat treatment refer to the result obtained from the heating to the maximum temperature of 40.9° C. and execution of eight times of high temperature-low temperature steps (the maximum and minimum temperatures of the heat treatment executed here are 40.9° C. and 39.4° C. respectively). Compared with the white column of the control group (without the use of the heat treatment of the present invention) in FIG. 5A, the cell viability of the portion of the neural living tissue after the heat treatment and hydrogen peroxide processing (as shown in the white column on the right side in FIG. 5A) is increased from 55% without the heat treatment to 70%. This is sufficient to prove that the heat treatment method of the present invention is able to promote the repair of the neural cells under the environment of high oxidative stress.

Figure 5B:
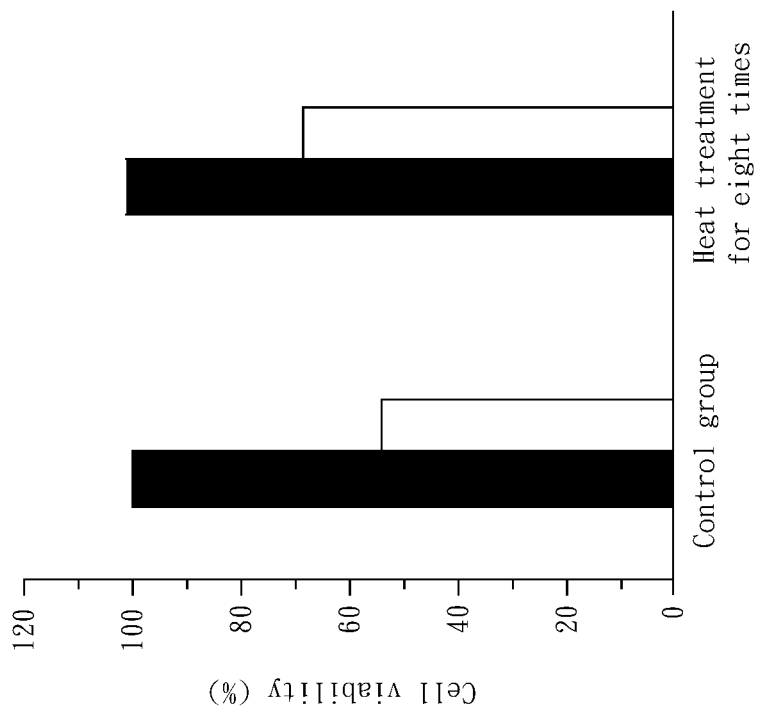
FIG. 5B is another cell viability diagram according to the first preferred embodiment of the present invention, showing the result of the human neural cells (SH-SY5Y) with/without application of hydrogen peroxide and heat treatment, and the maximum temperature of the heat treatment is 42° C.

Please refer to FIG. 2 again, in which the triangle symbols show another temperature curve, indicating a different result obtained from heat treatment executed with different temperatures in the first embodiment. In step S1) and step S3), the portion of the neural living tissue is heated and its temperature is 42° C. at the final time point, and the temperature at the final time point after cooling in step S2) is 40.3° C. Under such conditions, the result of eight times of heat treatment executed is as shown in FIG. 5B, wherein the black columns refer to the cell viability of human neural cells (SH-SY5Y) without the hydrogen peroxide treatment. From the comparison of the black columns in the control group and the heating group subject to eight times of heat treatment in FIG. 5B, it can be observed that the cell viability of the normal neural cells after the heat treatment of the present invention is unaffected, indicating that the heat treatment method of the present invention does not damage normal human neural cells (SH-SY5Y). In addition, compared with the white column of the control group (without the use of heat treatment of the present invention) in FIG. 5B, under the criteria where the maximum heating temperature is 42° C. (the maximum and minimum temperatures of the heat treatment executed here are 42.0° C. and 40.3° C. respectively), the cell viability of the portion of the neural living tissue after the heat treatment and the hydrogen peroxide processing (as shown by the white column on the right side of FIG. 5B) is increased from 55% without the heat treatment to 82%. This is sufficient to prove that the heat treatment method of the present invention is able to allow the neural cells under the high oxidative stress induced by hydrogen peroxide to increase the antioxidative capacity, thereby achieving the effect of neural repair.

Figure 6:
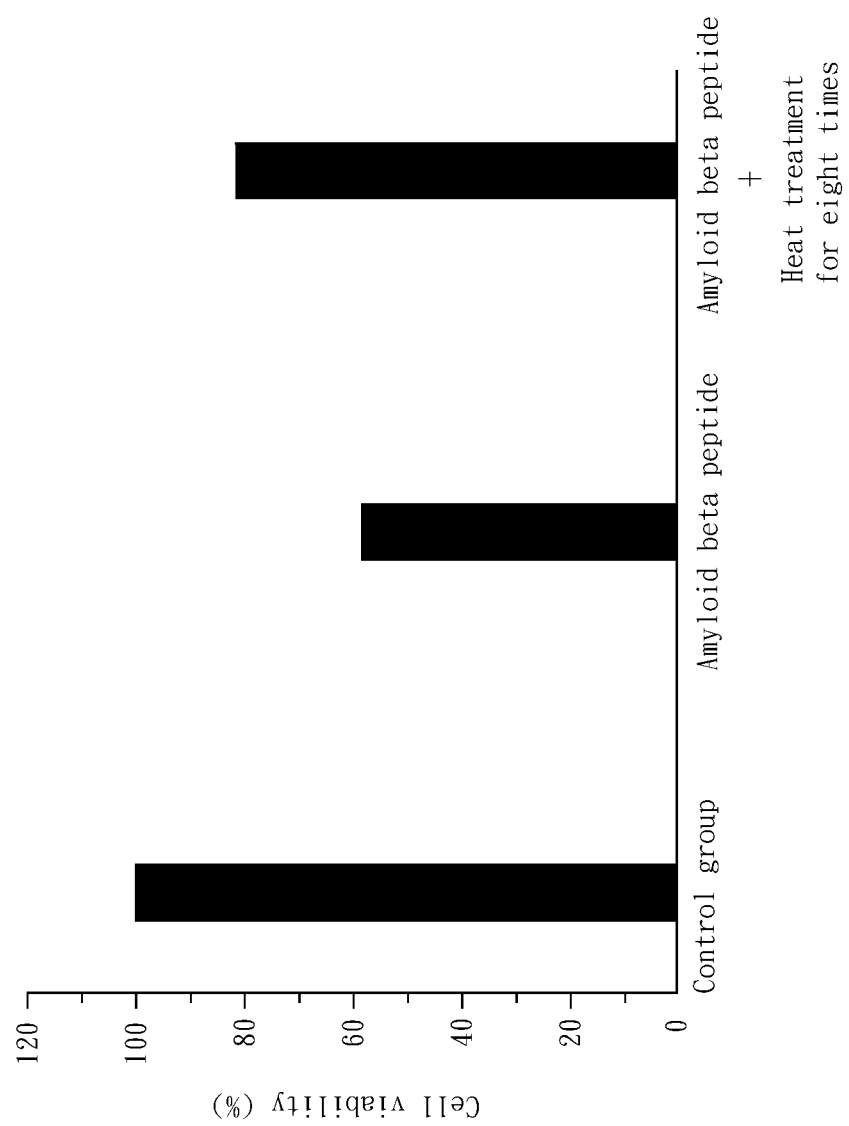
FIG. 6 is another cell viability diagram according to the first preferred embodiment of the present invention, showing the heat treatment result of the human neural cells (SH-SY5Y) after the treatment of amyloid beta peptide.

In addition, as shown in FIG. 6, the SH-SY5Y neural cells under degenerative state after amyloid beta peptide being used to treat the human neural cells (SH-SY5Y) are used as an example for illustration. Here, in step S1) and step S3), the temperature at the final time point for the heating of the neural living tissue is 42° C., and the temperature at the final time point for cooling in step S2) is 40.3° C. The above-mentioned heating condition is as shown by the temperature curve presented by the triangle symbols in FIG. 2. The result obtained from eight times of heat treatment under the aforementioned condition is as shown in FIG. 6, and it indicates that the viability of the SH-SY5Y neural cells after the treatment of amyloid beta peptide but without the eight times of heat treatment is only 57%. However, after executing eight times of heat treatment according to the method of the present invention on the SH-5Y5Y neural cells already treated by amyloid beta peptide, the cell viability of the damaged portion of the neural living tissue is significantly increased from 57% without the heat treatment to 82%, which is sufficient to prove that the method of the present invention is able to allow damaged neural cells to restore effectively.

In view of the above, the technique of the first embodiment is able to allow abnormal cells to be selectively restored under the condition where normal cells are not damaged.

As shown in FIG. 7 to FIG. 8A and FIG. 8B, according to a second preferred embodiment of the present invention, a method for applying heat to living tissue is provided. Its main concept is generally identical to the first embodiment, and the difference between the two relies in:

In step S1) and step S3), a predefined compound or natural complex is applied to the portion of the living tissue. In the second embodiment, the natural complex, propolis, is used as an example for illustration and its concentration is 0.3%. In addition, for the portion of the living tissue, the human pancreatic cancer cells (PANC-1) are used instead of the neural cells as an example for illustration. Furthermore, the living pancreatic cancer cells are also placed in the culture solution of petri dish in order to perform the heat treatment method of the present invention. During the actual operation in practice, since propolis is left in the petri dish after the application of the propolis in step S1), the cells are naturally remained under the application of propolis in step S2) and step 3).

Figure 7:
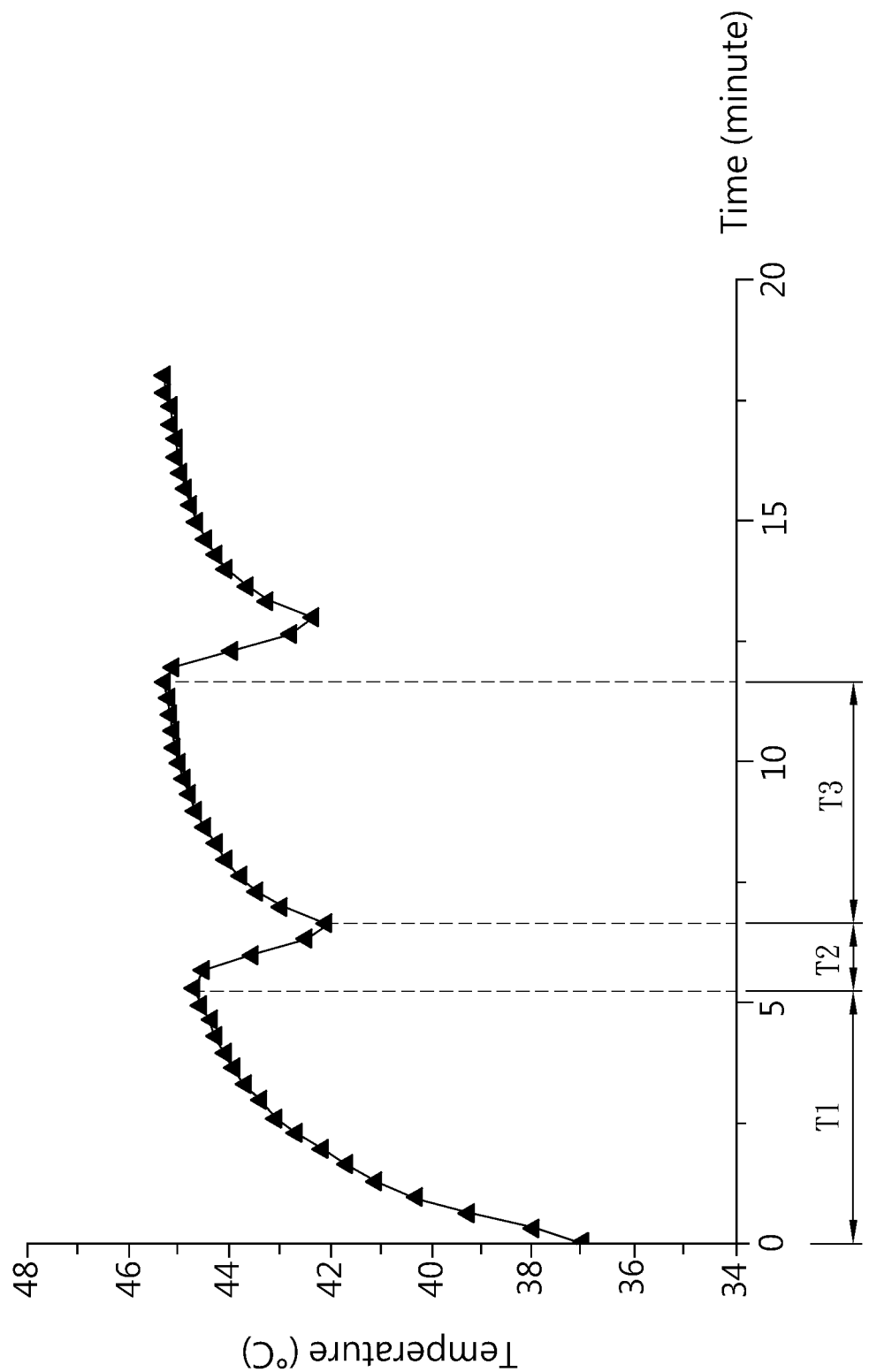
FIG. 7 is a temperature-time relation graph according to the second preferred embodiment of the present invention.
Figure 8:
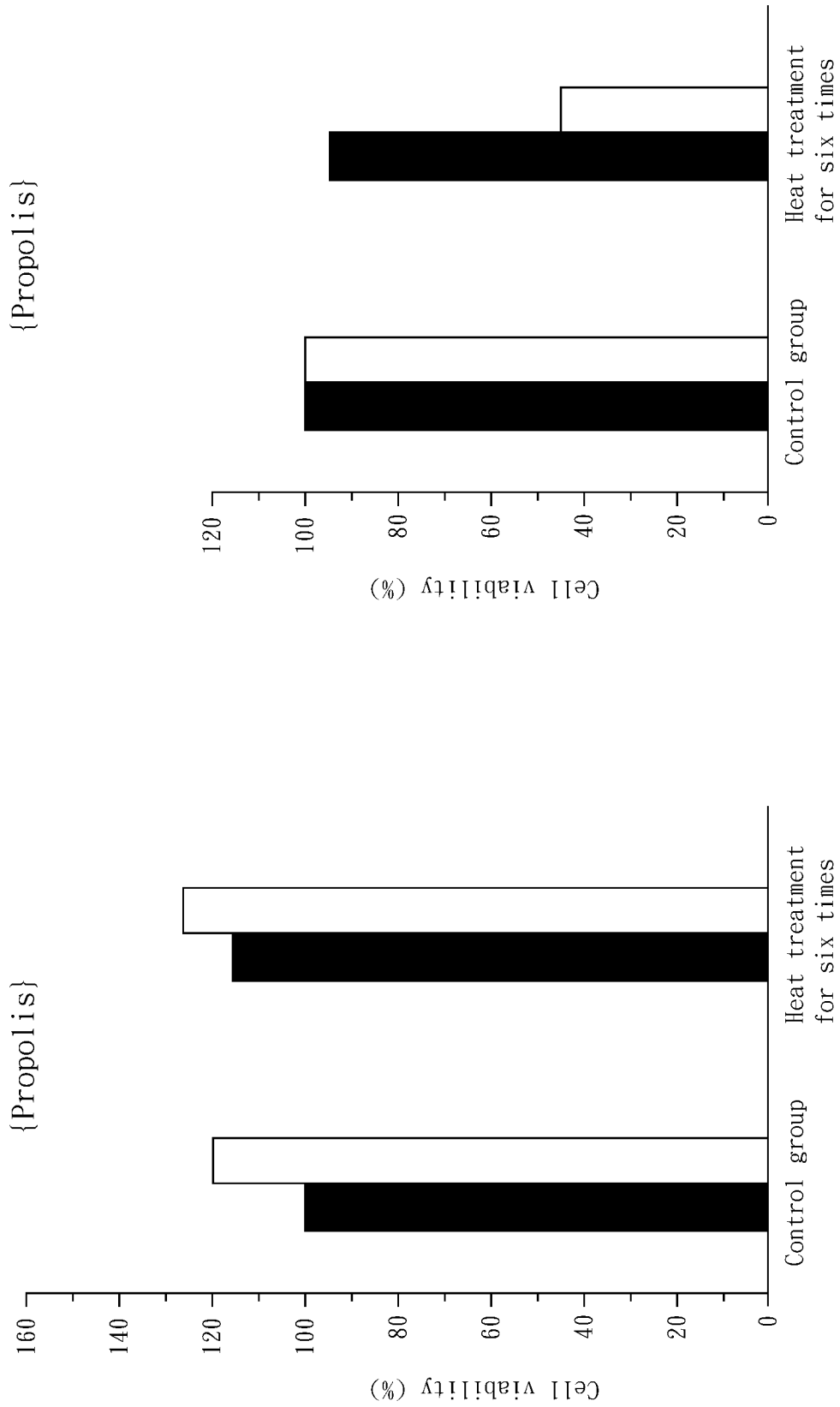
FIG. 8A is a cell viability diagram according to the second preferred embodiment of the present invention, showing the result of the normal human pancreatic cells (H6c7) with/without application of propolis and heat treatment.
FIG. 8B is a cell viability diagram according to the second preferred embodiment of the present invention, showing the result of the human pancreatic cancer cells (PANC-1) with/without application of propolis and heat treatment.

As shown in FIG. 7, in the second embodiment, the first time interval T1 and the third time interval T3 are 5 minutes, and the second time interval T2 is 1 minute.

As shown in FIG. 7, the temperature of the portion of the living tissue being heated at the final time point in step S1)

is close to 45° C., and the temperature of the portion of the living tissue being heated at the final time point in step S3) is 45° C. In addition, the temperature of the portion of the living tissue being cooled at the final time point in step S2) is 42° C. Under such condition where the heating temperature is close to 45° C., after the execution of six times of the high temperature-low temperature steps, i.e. one time of step S1) with five times of step S2) and step S3), the result is as shown in FIG. 8A and FIG. 8B. The black columns in FIG. 8A represent the results of the normal human pancreatic cells (H6c7) without the propolis treatment, and the white columns in FIG. 8A represent the results of the normal human pancreatic cells (H6c7) subject to 0.3% of propolis treatment. The control group represents the cells without the heat treatment, and the execution of heat treatment for six times refers to the result obtained from the application of six times of high temperature-low temperature steps of the heat treatment. FIG. 8A indicates that when normal human pancreatic cells are subject to the heat treatment according to the method of the present invention, the viability of the normal pancreatic cells is not affected to reduce by the heat treatment, meaning that the heat treatment of the present invention does not cause damages to normal human pancreatic cells. In FIG. 8B, the black columns represent the results for the viability of human pancreatic cancer cells (PANC-1) without the propolis treatment, and the white columns represent the results for the viability of human pancreatic cancer cells (PANC-1) subject to the propolis treatment. The control group represents the comparison group not subject to the heat treatment executed according to the method of the present invention, and the heat treatment for six times means to the result of six times of high temperature-low temperature steps. From FIG. 8B, it can be observed that after the execution of the heat treatment according to the method of the present invention, the cell viability of the pancreatic cancer cells without the propolis treatment is reduced from 100% to 95%, indicating that the cell viability remains generally the same. As for the cell viability of pancreatic cancer cells subject to the propolis treatment, it is reduced from 100% to 44% after the heat treatment. This result is sufficient to prove that the method of the present invention in conjunction with the use of appropriate natural complex is able to effectively cause the apoptosis of pancreatic cancer cells.

According to the above, it can be understood that the technique of the second embodiment is able to selectively cause the apoptosis of abnormal cells under the condition where normal cells are not damaged.

The remaining technical features and the achievable effects of the second embodiment are generally identical to the ones of the aforementioned first embodiment; therefore, details thereof are omitted hereafter.

Figure 9:
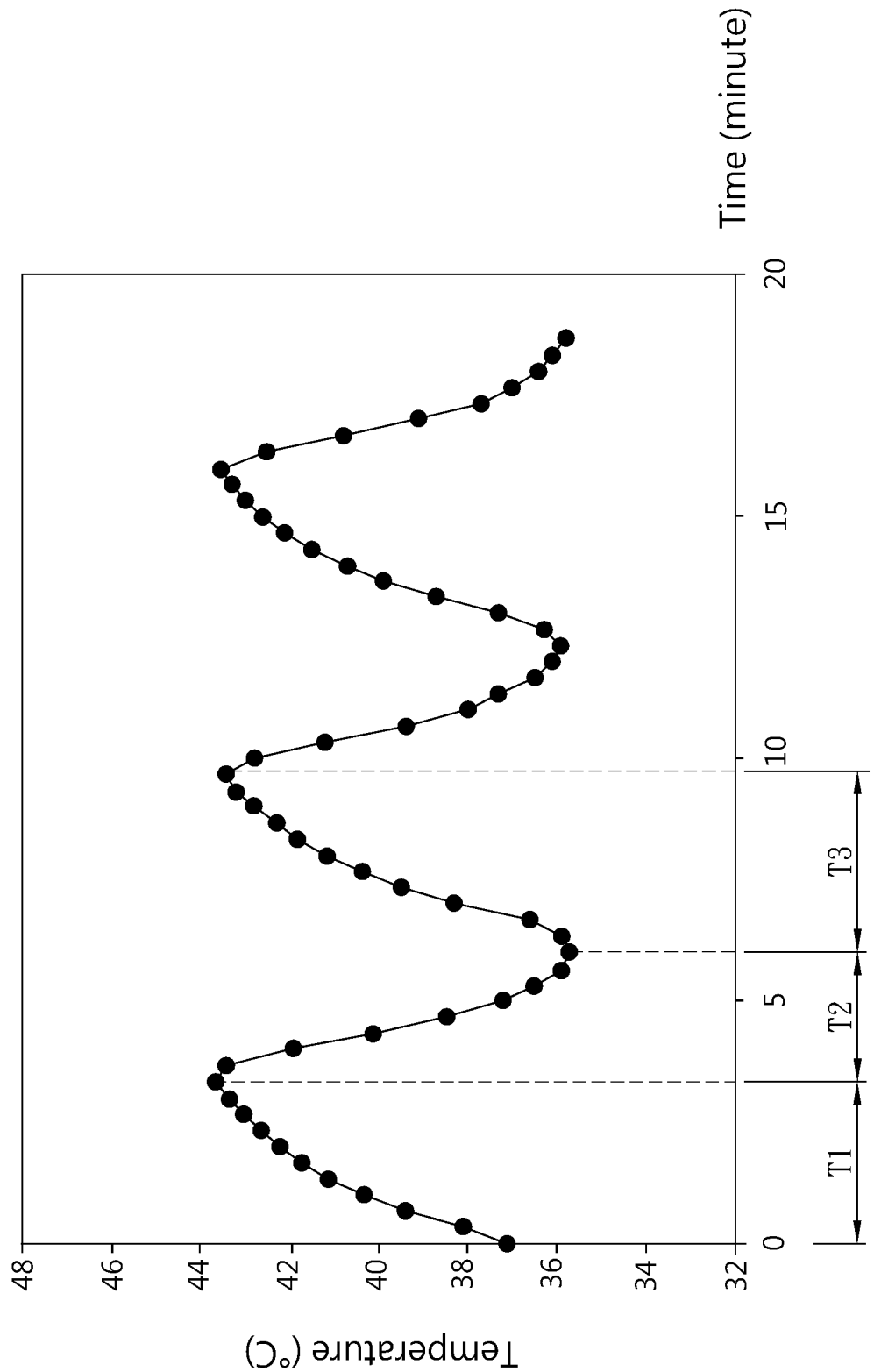
FIG. 9 is a temperature-time relation graph according to the third preferred embodiment of the present invention.
Figure 10B:
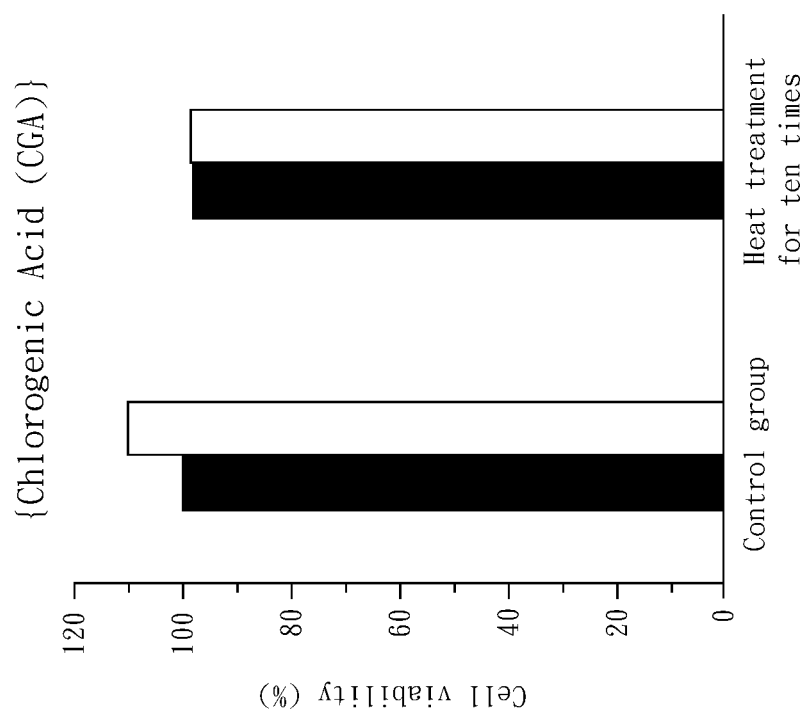
FIG. 10B is a cell viability diagram according to the third preferred embodiment of the present invention, showing the result of the human pancreatic cancer cells (PANC-1) with/without application of chlorogenic acid and heat treatment.
Figure 10A:
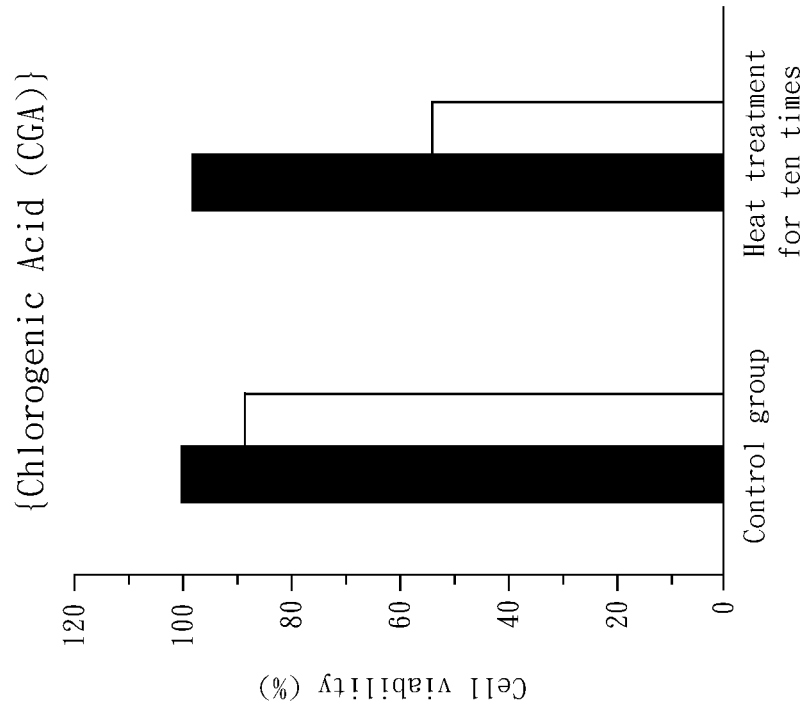
FIG. 10A is a cell viability diagram according to the third preferred embodiment of the present invention, showing the result of the normal human pancreatic cells (H6c7) with/without application of chlorogenic acid and heat treatment.
Figure 11:
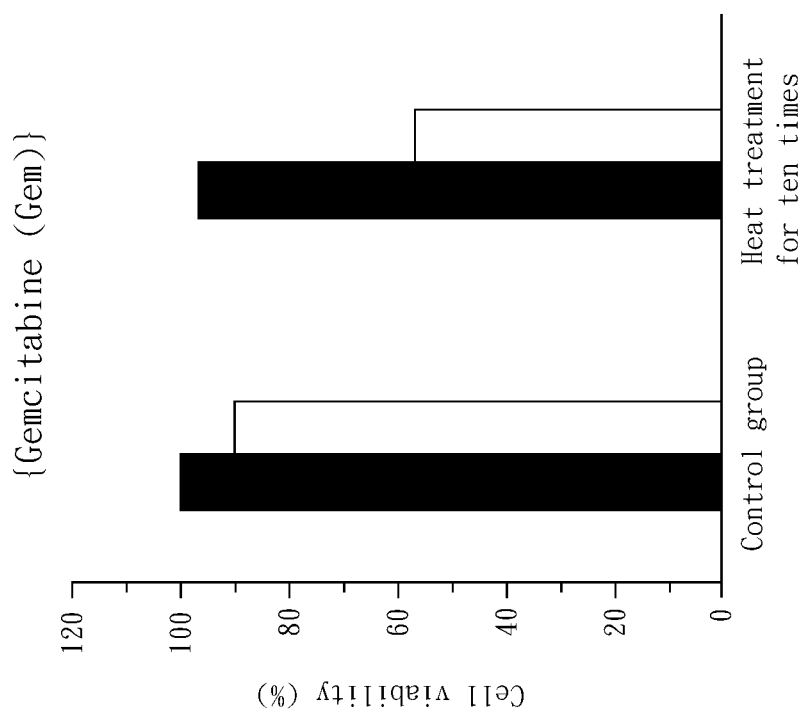
FIG. 11 is another cell viability diagram according to the third preferred embodiment of the present invention, showing the result of the human pancreatic cancer cells (PANC-1) with/without application of gemcitabine and heat treatment.

As shown in FIG. 9 to FIG. 11, according to a third preferred embodiment of the present invention, a method for applying heat to living tissue is provided. Its main concept is generally identical to the second embodiment, and the difference between the two relies in:

In the third embodiment, the predefined compound uses chlorogenic acid (CGA) as an example for illustration and its concentration is 200 μM. In addition, for the portion of the living tissue, the human pancreatic cancer cells (PANC-1) are used as an example for illustration. Furthermore, the living pancreatic cancer cells are also placed in the culture solution of petri dish in order to perform the heat treatment method of the present invention.

As shown in FIG. 9, in the third embodiment, the first time interval T1 and the third time interval T3 are 3 minutes, and the second time interval T2 is 2 minutes and 30 seconds. Such value for T2 is also smaller than the 5 minutes of the natural cooling time interval TM in the aforementioned first embodiment. Consequently, here, the problem associated with the interrupted transmission of biochemical signals and protein expressions leading to the apoptosis of cancer cells caused by an overly long period of relief can be prevented. In addition, in the third embodiment, for the low temperature step of step S2), the cooling is executed with a cooling method in order to allow the portion of the living tissue to be cooled at a relatively faster rate. Furthermore, at the end time point of the second time interval T2, the temperature of the portion of the living tissue is also lowered to below 37° C.

As shown in FIG. 9, in step S1) and step S3), the temperature at the final time point of the heated portion of the living tissue is 43.5° C., and the temperature at the final time point for the cooling in step S2) is approximately 36° C. Under such condition of heating temperature of 43.5° C., after the execution of ten times of high temperature-low temperature steps on the portion of the living tissue according to the method of the present invention, i.e. one time of step S1) with nine times of steps S2) and S3), the results are as shown in FIG. 10A and FIG. 10B. In FIG. 10A, the black columns represent the results of the normal human pancreatic cells (H6c7) without the CGA treatment, and the white columns represent the results of the normal human pancreatic cells (H6c7) subject to the 200 μM CGA treatment. The control group represents the cells without the heat treatment, and the execution of heat treatment for ten times refers to the result obtained from the application of ten times of high temperature-low temperature steps of the heat treatment. FIG. 10A indicates that when normal human pancreatic cells are subject to the heat treatment according to the method of the present invention, the cell viability of the normal pancreatic cells is unaffected, meaning that the heat treatment of the present invention does not damage normal human pancreatic cells. In FIG. 10B, the black columns represent the results for the viability of human pancreatic cancer cells (PANC-1) without the CGA treatment, and the white columns represent the results for the viability of human pancreatic cancer cells (PANC-1) subject to the CGA treatment. The control group refers to the comparison group not subject to the heat treatment according to the method of the present invention, and the execution of ten times of heat treatment refers to the result of the execution of ten times of high temperature-low temperature steps. As shown in FIG. 10B, it can be observed that after the use of the heat treatment according to the method of the present invention, the cell viability of the pancreatic cancer cells without the CGA treatment is reduced from 100% to 98%, and the cell viability indicates no significant change. Regarding the cell viability of pancreatic cancer cells with the CGA treatment, it is reduced from the cell viability of 88% without the heat treatment to 53% after the heat treatment. Such result is sufficient to prove that the method of the present invention in conjunction with appropriate compound is able to effectively cause the apoptosis of pancreatic cancer cells.

In the third embodiment, if the predefined compound is changed to gemcitabine (Gem) with the concentration of 5 μM and under the condition where the first time interval T1, the second time interval T2 and the third time interval T3 as well as the heating temperature and cooling temperature are the same as the ones in the aforementioned heat treatment of CGA, the result after the execution of ten times of high temperature-low temperature steps is as shown in FIG. 11. In FIG. 11, the black columns represent the results for the cell viability of human pancreatic cancer cells (PANC-1) without the Gem treatment, and the white columns represent the results for the cell viability of human pancreatic cancer cells (PANC-1) with the 5 µM Gem treatment. The control group refers to the comparison group without the heat treatment according to the method of the present invention. From FIG. 11, it can be observed that after the use of the heat treatment according to the method of the present invention, the cell viability of the pancreatic cancer cells without the Gem treatment is reduced from 100% to 96%. As for the cell viability of pancreatic cancer cells with the Gem treatment, the cell viability is reduced from 90% without the heat treatment to 55% after the heat treatment. Similarly, such result is sufficient to prove that the method of the present invention in conjunction with the use of appropriate compound is able to effectively cause the apoptosis of pancreatic cancer cells.

The remaining technical features and the achievable effects of the third embodiment are generally identical to the ones of the aforementioned first embodiment; therefore, details thereof are omitted hereafter.

Figure 12:
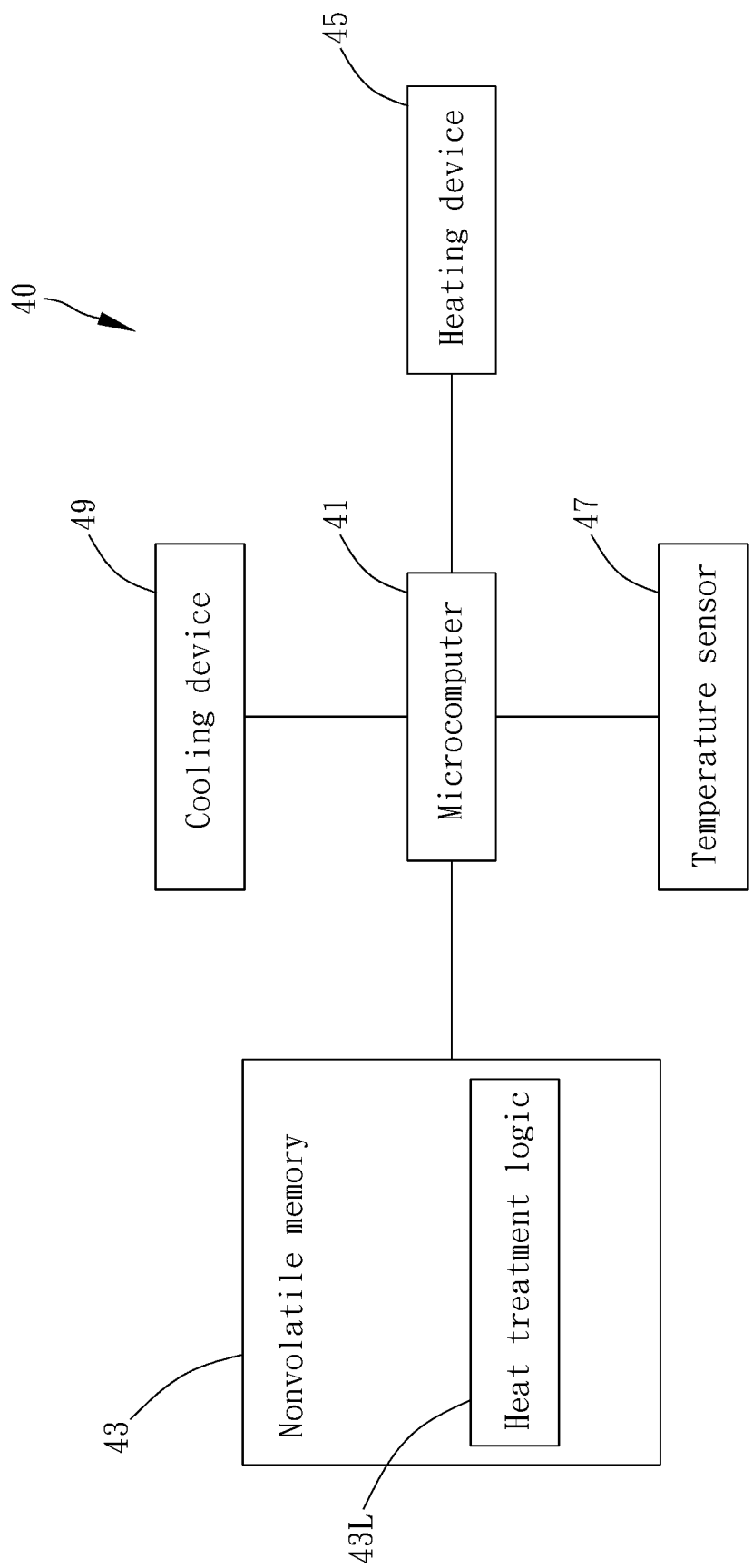
FIG. 12 is a circuit diagram according to the fourth embodiment of the present invention.

As shown in FIG. 12, according to a fourth preferred embodiment of the present invention, an apparatus 40 for applying heat to living tissue by using the heat treatment method mainly comprises a microcomputer 41, a nonvolatile memory 43, a heating device 45 and temperature sensor 47.

The nonvolatile memory 43 is electrically connected to the microcomputer 41. The nonvolatile memory 43 is stored with a heat treatment logic 43L in order to be executed by the microcomputer 41. The heat treatment logic 43L comprises the technical features of the aforementioned step S1) to step S3), and when the microcomputer 41 executes the heat treatment logic 43L, it executes the methods of the aforementioned step S1) to step S3), and it also controls the heating device 45 in heating the portion of the living tissue when there is a need to perform heating.

The heating device 45 is electrically connected to the microcomputer 41. During the actual practice, the heating device 45 can be selected to be one of a water bath device, a high intensity focused ultrasound (HIFU) device, an infrared device, a radio frequency electromagnetic wave device and a microwave device. In the aforementioned embodiments of the present invention, the water bath device is used as an example for illustration.

The temperature sensor 47 is electrically connected to the microcomputer 41, and it is used to detect the current temperature of the portion of the living tissue. During the actual practice, if the portion is located at the internal of the living tissue such that contact type of temperature measurement method cannot be used easily, then the temperature sensor 47 can be a device using a contactless method for temperature measurement, such as the known devices of ultrasonic temperature measurement device, magnetic resonance imaging (MRI) temperature measurement device etc., in order to measure the temperature of the portion at the internal of the living tissue.

It shall be noted that in the aforementioned low temperature step of step S2), if the method of natural cooling or reduction of heating power is used, then there is no need for the additional use of cooling method. However, if the cooling method is used for reducing the temperature, then it is necessary to additionally prepare a cooling device 49, and such cooling device 49 can be electrically connected to the microcomputer 41. When the microcomputer 41 executes the heat treatment logic 43L, it controls the cooling device 49 to perform the cooling process on the portion of the living tissue. During the actual operation, the cooling method typically uses a coolant or a temperature-controlled coolant circulating device to perform cooling on the living tissue via a contact method. Nevertheless, if the portion under cooling is at the internal of the living tissue, then in practice, it is necessary to perform cooling of the exterior of the living tissue or other tissues in contact, followed by using the heat conduction method to indirectly perform cooling on the portion of the living tissue.

The aforementioned four embodiments are provided as examples for illustration purpose only, which shall not be treated as limitation to the claim scope of the present invention. In addition, it shall be further noted that the duration of the first time interval T1 and the third time interval T3 can be different from each other depending upon the actual needs of the operator.

What is claimed is:

1. A method for applying heat to living tissue, comprising the following steps:
    S1) high temperature: in a first time interval, heat at least a portion of a living tissue, and maintain a temperature of the at least a portion of the living tissue between 39-46° C. within the first time interval; the first time interval being less than 30 minutes; wherein the at least a portion of the living tissue includes a plurality of normal cells and a plurality of abnormal cells;
    S2) low temperature: use an end-time point of the first time interval as a starting point of a second time interval, and cool the at least a portion of the living tissue in the second time interval; and a temperature of the least a portion of the living tissue in the second time interval being lower than a maximum temperature in the first time interval; and a time period required for the at least a portion of the living tissue to be cooled from 45° C. to 39° C. via a natural cooling method under a criteria where an environmental temperature is between 36.5-37° C. being defined to be a natural cooling time interval; the second time interval being shorter than the natural cooling time interval; and
    S3) high temperature: use an end-time point of the second time interval as a starting point of a third time interval, and heat the at least a portion of the living tissue in the third time interval in order to increase a temperature of the at least a portion of the living tissue, and maintain the temperature of the at least a portion of the living tissue to be between 39-46° C. in the third time interval; the third time interval being less than 30 minutes; the second time interval being shorter than the first time interval, and the second time interval being shorter than the third time interval.

2. The method for applying heat to living tissue according to claim 1, wherein: a temperature of the at least a portion of the living tissue at the end of the first time interval in step S1) is higher than a temperature of the at least a portion of the living tissue at the end of the second time interval in step S2) by more than 0.5° C.

3. The method for applying heat to living tissue according to claim 1, further comprising: repetitively execute step S4): repetitively execute step S2) and step S3) sequentially and maintain a cycle of one time of the low temperature step and one time of the high temperature step.

4. The method for applying heat to living tissue according to claim 1, wherein: in step S1), the first time interval is not less than 30 seconds; in step S2), the second time interval is not less than 5 seconds; in step S3), the third time interval is not less than 30 seconds.

5. The method for applying heat to living tissue according to claim 1, wherein: in step S1) and step S3), apply a predefined compound or natural complex to the at least a portion of the living tissue.

6. The method for applying heat to living tissue according to claim 5, wherein: a temperature of the at least a portion of the living tissue at the end of the first time interval in step S1) is higher than a temperature of the at least a portion of the living tissue at the end of the second time interval in step S2) by more than 0.5° C.

7. The method for applying heat to living tissue according to claim 5, further comprising: repetitively execute step S4): repetitively execute step S2) and step S3) sequentially and maintain a cycle of one time of the low temperature step and one time of the high temperature step.

8. The method for applying heat to living tissue according to claim 5, wherein: in step S1), the first time interval is not less than 30 seconds; in step S2), the second time interval is not less than 5 seconds; in step S3), the third time interval is not less than 30 seconds.

* * * * *